United States Patent [19]

Young et al.

[11] Patent Number: 5,362,757
[45] Date of Patent: Nov. 8, 1994

[54] COMPOSITION AND METHOD CONTAINING OPTICALLY PURE (S) METOPROLOL

[75] Inventors: James W. Young, Still River; Timothy J. Barberich, Concord, both of Mass.

[73] Assignee: Sepracor, Inc., Marlborough, Mass.

[21] Appl. No.: 976,676

[22] Filed: Nov. 16, 1992

Related U.S. Application Data

[63] Continuation of Ser. No. 670,995, Mar. 18, 1991, abandoned.

[51] Int. Cl.$^5$ ............................................. A61K 31/135
[52] U.S. Cl. ....................................... 514/652; 514/821; 514/929
[58] Field of Search ........................... 514/652, 821, 929

[56] References Cited

U.S. PATENT DOCUMENTS 4,945,114  7/1990  Franke et al. ....................... 514/652

OTHER PUBLICATIONS

CA 100(25):203346y, Lundin et al., 1984.
Michel Boucher, et al., *Br. J. Pharmac.* 89:119–127 (1986).
James A. Nathanson, *The Journal of Pharmacological and Experimental Therapeutics*, 245(1):94–101 (1988).
Stephen Toon, et al., *Clin Pharmacol. Ther.*, 43(3):283–289 (1988).
G. Wahlund, et al., *Br. J. Pharmacol.* 99:592–596 (1990).
Noburu Toda, et al., *The Journal of Pharmacology and Experimental Therapeutics* 207(2):311–319 (1978).
L. Bradley and S. A. Doggrell, *Arch. Int. Pharmacodyn.* 270:61–78 (1984).
CA 112(17):151274z, Wahlund et al., 1990.

*Primary Examiner*—Marianne M. Cintins
*Assistant Examiner*—Kimberly R. Jordan
*Attorney, Agent, or Firm*—Hamilton, Brook, Smith & Reynolds

[57] ABSTRACT

Optically pure (S) metoprolol, which is substantially free of the (R) enantiomer, is a potent beta-blocker for treating myocardial infarction and for relieving the symptoms of angina pectoris, cardiac arrhythmia and hypertension in individuals. A method is disclosed utilizing the optically pure (S) configurational enantiomer of metoprolol for treating cardiovascular disorders while reducing undesirable side effects associated with the administration of beta-blockers.

8 Claims, No Drawings

COMPOSITION AND METHOD CONTAINING OPTICALLY PURE (S) METOPROLOL

This is a continuation of copending application Ser. No. 07/670,995 filed on Mar. 18 1991, now abandoned.

BACKGROUND

Metoprolol is a drug belonging to the general class of compounds known as beta-blockers. Beta-blockers are beta-selective adrenoreceptor blocking agents, and include well-known commercial products such as propanolol and atenolol. Several members of this drug class are known to be useful in treatment of hypertension, angina pectoris, and myocardial infarction.

Although the mechanism of the antihypertensive effect of metoprolol (and other β-blockers) is not known with certainty, a number of mechanistic possibilities have been advanced, including: the suppression of endogenous catecholamines at cardiac adrenergic neuron sites; a central effect leading to reduced sympathetic outflow to the periphery; and suppression of rennin activity.

The effectiveness of metoprolol in treatment of angina pectoris is likely to be associated with its tendency to reduce the oxygen requirements of the heart at various levels of effort. This effect results from blockage of catecholamine-induced increases in heart rate, blood pressure, and in velocity and extent of myocardial contraction.

Metropolol is regarded to be a relatively selective β-blocker. That is, it has a preferential effect on β1 adrenoreceptors which are predominant in cardiac muscle. This selectivity is not absolute, however, and metoprolol also exhibits activity on β2 adrenoreceptors located in bronchial and peripheral vascular tissue.

Metropolol is a racemic mixture. That is, it is a mixture of optical isomers, called enantiomers. Enantiomers are structurally similar compounds which differ only in that one isomer is a configurational mirror image of the other and the mirror images cannot be superimposed. This phenomenon is known as chirality. Although structurally similar, enantiomers can have profoundly different effects in biological systems; one enantiomer is often biologically active while the other has little or no biological activity at all.

SUMMARY OF THE INVENTION

The present invention relates to a method of treating cardiovascular disorders, including angina pectoris, cardiac arrhythmia, hypertension or myocardial infarction in an individual comprising administering to the individual a therapeutic amount of the (S) enantiomer of metoprolol which is substantially free of the (R) enantiomer. The method is useful in treating cardiovascular disorders while reducing or avoiding undesirable side effects such as: central nervous system effects (tiredness, dizziness, short-term memory loss, headache, nightmares and insomnia); cardiovascular effects (bradycardia, cardiac depression, cold extremities, palpitations, and peripheral edema); respiratory effects (shortness of breath, wheezing, dyspnea); hypersensitive reactions (pruritis, rash); and miscellaneous effects such as vertigo, decreased libido and hallucinations which are associated in whole or in part with the (R) enantiomer. For beta-blocking drugs, it is important to have a beta-blocking composition which also minimizes these side effects. A composition containing the (S) isomer of metoprolol is particularly useful because the (S) isomer exhibits both of these desired characteristics.

Of particular importance is the fact that for patients suffering from cardiac failure along with hypertension, or angina pectoris, further cardiac depression caused by bradycardia and decreased myocardial contractility can lead to a worsening of their overall condition. Also these latter effects can lead gradually to cardiac failure in patients who have not exhibited this problem. In the method of the present invention, bradycardia and decreased myocardial contractility are less pronounced than when metoprolol is administered as the racemic mixture.

The present method provides a safe, highly effective method for treating the cardiac disorders associated with hypertension, angina pectoris or myocardial infarction.

DETAILED DESCRIPTION OF THE INVENTION

The present invention relies on the beta-blocking activity of the S configurational enantiomer of metoprolol, referred to as (S) metoprolol, to provide enhanced beta-blocking activity, for example, in treatment of hypertension, angina pectoris or myocardial infarction, without many of the undesirable side effects associated with beta-blockers, i.e., central nervous system effects, cardiovascular effects, respiratory effects, and miscellaneous effects such as vertigo, decreased libido and hallucinations. In the present method, (S) metoprolol, which is substantially free of its (R) enantiomer, is administered alone, or in combination with other drugs in adjunctive treatment, to an individual suffering from a cardiovascular disorder, such as heart disease, angina or hypertension. "(S) metoprolol" as used herein refers to the S configurational isomer of 1-(isopropylamino)-3-[p-(2-methoxyethyl)phenoxy]-2-propanol, and also pharmaceutically acceptable salts, such as the tartrate salt, of the compound. The term "substantially free of the (R) enantiomer" as used herein means that the composition contains at least 90% by weight (S) metoprolol and 10% by weight or less of (R) metoprolol.

Prior to this invention, metoprolol has been administered as the racemic mixture. However, by the method of the present invention (S) metoprolol is administered substantially free of the (R) enantiomer. (R) metoprolol can contribute to adverse side effects in some individuals without any desired therapeutic effect. Thus, it is desirable to use the pure (S) isomer in cardiovascular applications, because it is much more cardioactive than the (R) isomer, and because it minimizes activity associated with the undesirable side effects of the (R) isomer.

In the present method, (S) metoprolol is administered to an individual suffering from a cardiovascular disorder, such as angina pectoris, cardiac arrhythmia, hypertension or myocardial infarction. For example, (S) metoprolol is administered therapeutically to an individual after a heart attack, or to reduce or ameliorate hypertension and regulate heart beat or to reduce the symptoms of angina pectoris. Alternatively, (S) metoprolol can be administered prophylactically to reduce the probability of occurrence of a heart attack.

Metropolol, like propranolol and certain other beta-blockers, undergoes substantial first-pass metabolism by the liver before entering the circulatory system. Approximately 40–50% of the administered oral dose appears intact in the systemic circulation. Shetty and Nelson (*J. Med. Chem.*, 31, 55–59, 1988) have studied the stereochemical aspects of the metabolic processing of metoprolol and demonstrated that the primary metabolic process, benzylic hydroxylation, is effected stereoselectively. Both enantiomers of metoprolol are hydroxylated to form metabolites of the (R) configuration at the new benzylic (1′) chiral center. (S) metoprolol is hydroxylated with a significantly higher degree of stereoselectivity than (R) metoprolol (R/S ratio at the new benzylic (1′) chiral center of 26 vs. 9.4).

The high degree of first-pass metabolism of metoprolol requires the administration of higher doses by the oral route than would otherwise be required. One aspect of the present invention, therefore, is that the (S) metoprolol enantiomer is sufficiently potent that it can be administered by means that avoid such first-pass metabolism (for example transdermally), thereby resulting in a systemic concentration in the therapeutically effective range with a substantial reduction in the needed dosage. Racemic metoprolol is not conveniently administered in such forms, because of the substantially higher doses involved.

Delivery methods that offer such advantages include but are not limited to transdermal patches, topical creams and ointments, electrically-stimulated transdermal delivery systems and metered injection delivery systems.

Other possible routes of drug administration are orally, by subcutaneous or other injection, intravenously, parenterally, rectally or via by sustained release methods, e.g., an implanted reservoir containing (S) metoprolol. The form in which the drug will be administered (e.g., powder, tablet, capsule, solution, emulsion) will depend on the route by which it is administered. The quantity of the drug to be administered will be determined on an individual basis, and will be based at least in part on consideration of the individual's size, the severity of the symptoms to be treated and the result sought. In general, quantities of (S) metoprolol sufficient to treat hypertension, angina pectoris, or myocardial infarction will be administered.

Racemic metoprolol is usually administered in doses of 100–450 mg per day, in single or divided doses. In the method of the present invention, doses of (S) metoprolol are in the range of 50–300 mg daily when administered orally. Dosages of 2–100 mg daily may be admininstered by methods which avoid first-pass hepatic metabolism, and preferably doses in the range of 5–25 mg daily.

In the method of the present invention, (S) metoprolol can be administered along with one or more other drugs. For example, other anti-hypertensive agents, such as thiazide-type diuretics, hydralazine, prazosin, and alpha-methyl dopa, can be given with or in close temporal proximity to administration of (S) metoprolol. The two (or more) drugs ((S) metoprolol and another drug) can be administered in one composition or as two separate entities. For example, they can be administered in a single capsule, tablet, powder, liquid, etc. or as individual compounds. The components included in a particular composition, in addition to (S) metoprolol and another drug or drugs, are determined primarily by the manner in which the composition is to be administered. For example, a composition to be administered orally in tablet form can include, in addition to the drugs, a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the combination of drugs and, optionally, an emulsifying agent, a flavoring agent and/or a coloring agent.

In general, according to the method of the present invention, (S) metoprolol, alone or in combination with another drug(s), is administered to an individual periodically as necessary to reduce or ameliorate symptoms of hypertension, angina pectoris or myocardial infarction while reducing or avoiding undesirable side effects associated with beta-blockers, including cardiac, central nervous system and respiratory effects. The length of time during which the drugs are administered and the dosage will depend on the disorder being treated, the type and severity of the symptoms, and the physical condition of the individual being treated.

The invention is further illustrated by the following example. This example is not intended to be limiting of the invention in any way.

EXAMPLE 1

PREPARATION OF (S) METOPROLOL

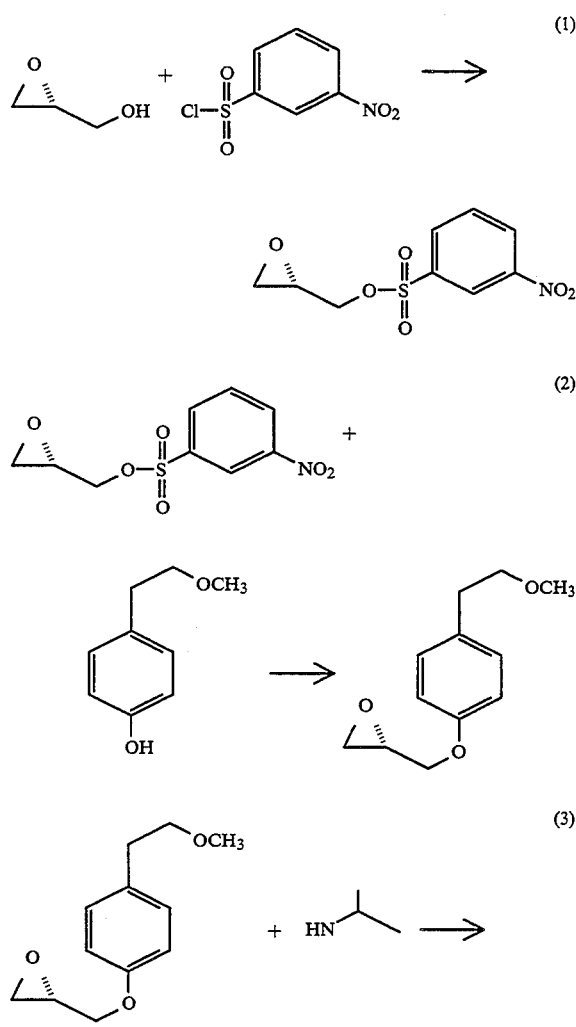

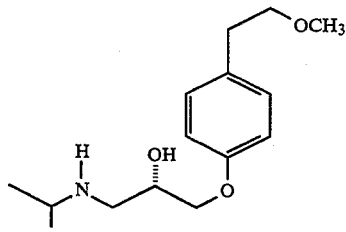

Preparation of S-Glycidyl m-Nitrobenzenesulfonate reaction 1):

A solution of R-glycidol and triethylamine in toluene was cooled with ice water (ca. 5° C.). m-Nitrobenzenesulfonyl chloride was added in portions while maintaining the temperature below 10° C. During the addition, a white precipitate (triethylamine hydrochloride) was formed. The mixture was stirred at room temperature for 22 hours. The mixture was then diluted with a small volume of ethyl acetate and filtered. The solid residue was washed thoroughly with ethyl acetate. The filtrate was then concentrated to dryness to give a yellow oil which on standing and cooling became a solid. The solid was recrystallized twice from ethyl acetate/hexane until the optical rotation did not change.

Preparation of p-(S-Glycidyloxy)-Methoxyethylebenzene (reaction 2);

Dry dimethylformamide (DMF) is cooled to ca. 5° C. with ice-water. Potassium t-butoxide is then added to form a solution. p-Hydroxy-methoxyethylbenzene in dry DMF is then slowly added at 5°-10° C. with vigorous stirring. The resulting mixture is then warmed to room temperature and stirred for a number of hours before being cooled back to 5° C. with ice-water. S-Glycidyl m-nitrobenzenesulfonate in DMF is then slowly added. After the addition, the mixture is stirred while allowing it to warm to room temperature. The reaction is then adjusted to neutral pH with NaH$_2$PO$_4$. The mixture is filtered and the residue washed with DMF. The combined filtrate is then concentrated in vacuo and poured into saturated NaCl solution at 5° C. with stirring. The resulting solid is collected by filtration and dried to give the title compound as a wet solid. The product is used without further purification in the next reaction.

Preparation of (S) Metoprolol (reaction 3):

The wet solid from the above reaction is added to water followed by isopropylamine. The suspension is heated to reflux and stirred for a number of hours. The reaction is followed by HPLC. The reaction is then cooled to room temperature and the excess isopropylamine removed by distillation. The resulting mixture is then saturated with NaCl. A solution of NaOH is then added to make the mixture 2% in NaOH. The mixture is stirred, then cooled to 5° C. and filtered. The solid is washed with water and dried in vacuo to give the title compound.

Equivalents

Those skilled in the art will recognize, or be able to ascertain, using no more than routine experimentation, many equivalents to the specific embodiments of the invention described herein. Such equivalents are intended to be encompassed in the scope of the following claims.

What is claimed is:

1. A method of treating a cardiovascular disorder in an individual and reducing undesirable side effects associated with the administration of racemic metoprolol, comprising administering to the individual a therapeutically effective amount of (S) metoprolol, which is substantially free of (R) metoprolol.

2. A method of claim 1 wherein the cardiovascular disorder is hypertension, cardiac arrhythmia, angina pectoris or myocardial infarction.

3. A method of claim 1 wherein the amount of (S) metoprolol in the composition is greater than about 90% by weight.

4. A method of claim 3 wherein the amount of (S) metoprolol in the composition is greater than 99% by weight.

5. A method of claim 1 comprising administering to the individual up to about 300 mg of (S) metoprolol per day.

6. A method of claim 1 wherein said therapeutically effective amount of (S) metoprolol is administered by a delivery means selected from the group consisting of transdermal patches, topical creams, topical ointments, electrically-stimulated transdermal delivery systems and metered injected delivery systems.

7. A method of treating a cardiovascular disorder in an individual and reducing undesirable side effects associated with the administration of racemic metoprolol, comprising administering to the individual a therapeutically effective amount of a composition containing (S) metoprolol and at least one other anti-hypertensive drug.

8. A method of claim 7 wherein the other anti-hypertensive drug is selected from the group consisting of thiazide-type diuretics, hydralazine, prazosin and alpha-methyldopa.

* * * * *